US012582340B2

(12) United States Patent
Pederson et al.

(10) Patent No.: US 12,582,340 B2
(45) Date of Patent: Mar. 24, 2026

(54) ELECTRODE WITH PROTECTED IMPEDANCE REDUCTION COATING

(71) Applicants:St. Jude Medical, Cardiology Division, Inc., St. Paul, MN (US); Brian Pederson, Selma, TX (US); Greg Olson, Elk River, MN (US)

(72) Inventors: Brian Pederson, Selma, TX (US); Greg Olson, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 259 days.

(21) Appl. No.: 18/279,787

(22) PCT Filed: Feb. 28, 2022

(86) PCT No.: PCT/US2022/018199
§ 371 (c)(1),
(2) Date: Aug. 31, 2023

(87) PCT Pub. No.: WO2022/187161
PCT Pub. Date: Sep. 9, 2022

(65) Prior Publication Data
US 2024/0138736 A1 May 2, 2024

Related U.S. Application Data

(60) Provisional application No. 63/156,030, filed on Mar. 3, 2021.

(51) Int. Cl.
| | |
|---|---|
| *A61B 5/287* | (2021.01) |
| *A61B 5/00* | (2006.01) |
| *A61B 18/14* | (2006.01) |
| *A61B 17/00* | (2006.01) |
| *A61B 18/00* | (2006.01) |

(52) U.S. Cl.
CPC ............ *A61B 5/287* (2021.01); *A61B 5/6858* (2013.01); *A61B 18/1492* (2013.01);
(Continued)

(58) Field of Classification Search
CPC .... A61B 2562/125; A61B 2018/00107; A61B 2018/00267; A61B 2018/00351;
(Continued)

(56) References Cited

U.S. PATENT DOCUMENTS

| | | |
|---|---|---|
| 10,188,348 B2 | 1/2019 | Al-Ali et al. |
| 11,497,546 B2 | 11/2022 | Nott et al. |

(Continued)

FOREIGN PATENT DOCUMENTS

| | | |
|---|---|---|
| EP | 1169975 A1 | 1/2002 |
| JP | 2020-124582 A | 8/2020 |

(Continued)

OTHER PUBLICATIONS

Boehler C., Oberueber, F., Schlabach S., Stieglitz, T., Asplund, A. Long-Term Stable Adhesion for Conducting Polymers in Biomedical Applications: IrOx and Nanostructured Platinum Solve the Chronic Challenge, ACS Appl. Mater. Interfaces 2017, 9, 1, 189-197 (Year: 2017).*

(Continued)

*Primary Examiner* — Eun Hwa Kim
(74) *Attorney, Agent, or Firm* — Wiley Rein LLP

(57) ABSTRACT

A catheter includes a shaft including a proximal end and a distal end, an electrical conductor coupled to the catheter, and an electrode coupled to the electrical conductor. The electrode includes at least one recessed portion, and an impedance reduction layer disposed in the at least one recessed portion. The impedance reduction layer has a thickness less than a depth of the recessed portion.

19 Claims, 11 Drawing Sheets

(52) U.S. Cl.
CPC .............. *A61B 2017/00526* (2013.01); *A61B 2018/00107* (2013.01); *A61B 2018/00267* (2013.01); *A61B 2018/00351* (2013.01); *A61B 2018/00577* (2013.01); *A61B 2018/00839* (2013.01); *A61B 2562/0209* (2013.01); *A61B 2562/125* (2013.01)

(58) Field of Classification Search
CPC ........... A61B 2018/00577; A61B 2018/00839; A61B 2018/00077; A61B 2018/0016; A61B 2018/00357; A61B 2018/1467; A61B 18/1492; A61B 5/287; A61B 5/6858
See application file for complete search history.

(56) References Cited

U.S. PATENT DOCUMENTS

| | | | | |
|---|---|---|---|---|
| 2009/0171187 | A1* | 7/2009 | Gerhart | A61B 5/283 |
| | | | | 606/41 |

| | | | | |
|---|---|---|---|---|
| 2013/0274736 | A1 | 10/2013 | Garrison | |
| 2014/0067031 | A1* | 3/2014 | Petersen | B23K 26/362 |
| | | | | 607/116 |
| 2015/0366508 | A1 | 12/2015 | Chou et al. | |
| 2018/0132790 | A1* | 5/2018 | Yao | A61N 1/0553 |
| 2019/0125440 | A1* | 5/2019 | Oliverius | A61B 18/1492 |
| 2019/0159833 | A1* | 5/2019 | Sutermeister | B23K 26/355 |
| 2022/0310282 | A1* | 9/2022 | Narayan | H01B 13/003 |

FOREIGN PATENT DOCUMENTS

| | | |
|---|---|---|
| WO | 94/16618 A1 | 8/1994 |
| WO | 2014/036439 A2 | 3/2014 |
| WO | 2019130832 A1 | 7/2019 |
| WO | 2021/001772 A1 | 1/2021 |

OTHER PUBLICATIONS

International Search Report and Written Opinion for International Application No. PCT/US2022/018199 mailed Jun. 8, 2022.

* cited by examiner

Pattern 1 - Plumes

Pattern 2 - Lines

Pattern 3 - Spots/Bursts

ELECTRODE WITH PROTECTED IMPEDANCE REDUCTION COATING

CROSS-REFERENCE TO RELATED APPLICATIONS

This application claims the benefit of and priority to U.S. Provisional Patent Application No. 63/156,030, filed Mar. 3, 2021, which is incorporated herein by reference its entirety.

BACKGROUND OF THE INVENTION

The instant disclosure relates to catheters, such as catheters for diagnosis or treatment of various medical conditions.

Catheters have been used for cardiac medical procedures for many years. Catheters can be used, for example, to diagnose and treat cardiac arrhythmias, while positioned at a specific location within a body that is otherwise inaccessible without a more invasive procedure. In general, mapping or diagnostic catheters can be used for diagnosing electrophysiology and generating three-dimensional models of tissue within the body. Other catheters, such as ablation catheters, can be used for treatment of some cardiac arrhythmias. Some catheters are configured to perform both mapping and ablation functions. In relation to mapping catheters, a tip portion of the catheter often has one or more electrodes for measuring electrophysiological signals (e.g., bio signals) within tissue. Various configurations of mapping catheters exist. Some mapping catheters have a single electrode for performing electrophysiological measurements whereas other mapping catheters can include a plurality of electrodes, such as an array of electrodes for collecting simultaneous measurements at various locations along the tissue. It can be desirable to increase the number of electrodes on the catheter in order to collect a greater amount of measurement data. In some instances, the collection of simultaneous data can also be advantageous for mapping and diagnosis purposes.

Because of geometrical confines within the body, both the placement of electrodes and use of an increased number of electrodes on a catheter can create challenges. Reducing the size and spacing of the electrodes can provide for an increase in the number and density of electrodes on the catheter. However, reducing the size of the electrodes correspondingly reduces the surface area of the electrodes for collecting electrophysiological measurement. As the size of the electrodes decreases, the electrical performance of the electrodes can be affected in some instances. Electrodes can be coated with impedance reduction layers to reduce impedance. Such layers can be prone to wear. The foregoing discussion is intended only to illustrate the present field and should not be taken as a disavowal of claim scope.

SUMMARY OF THE INVENTION

One embodiment relates to a catheter. The catheter includes a shaft including a proximal end and a distal end, an electrical conductor, and an electrode coupled to the electrical conductor. The electrode includes at least one recessed portion and an impedance reduction layer disposed in the at least one recessed portion. The impedance reduction layer has a thickness less than a depth of the recessed portion.

Another embodiment relates to a catheter for providing or receiving an electrical signal within a body. The catheter includes a substrate and an electrode. The electrode is disposed at a distal end of the catheter. The electrode includes an impedance reduction layer and a conductive material disposed above the substrate. The conductive material has at least one recessed portion, and the impedance reduction layer is disposed in the at least one recessed portion so that at least a portion of the conductive material above the at least one recessed portion protects the impedance reduction layer from abrasion.

Another embodiment relates to a method of making a catheter. The method includes coupling an electrical conductor and an electrode to the catheter, providing at least one recessed portion in the electrode, and disposing an impedance reduction layer in the at least one recessed portion of the electrode. The impedance reduction layer has a thickness less than a depth of the recessed portion.

In some embodiments, the at least one recessed portion is provided by masking at a location of the at least one recessed portion and plating a remaining portion of the electrode to form a cup-like structure. The remaining portion is exposed after masking at the location. In some embodiments, the electrode is formed on a flexible substrate and masking at the location uses a flexible tape.

Some embodiments relate to a catheter including a shaft including a proximal end and a distal end, an electrical conductor, a substrate including an electrode disposed on a top surface of the substrate and coupled to the electrical conductor, and a protective layer. The electrode includes an impedance reduction layer, and the protective layer is disposed above the top surface of the substrate. The protective layer has an opening exposing at least part of the electrode and is thicker than the electrode.

In some embodiments, the electrode comprises a repeating pattern of the recessed portion. In some embodiments, the recessed portion is formed by laser etching. In some embodiments, the recessed portion is formed using a raised edge of metal material. In some embodiments, the electrode is a ring electrode on a mapping catheter. In some embodiments, the electrode is disposed on a flex circuit. In some embodiments, the electrode is an ablation electrode.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Several embodiments of an electrode (including but not limited to an electrode for a flexible, high-density mapping catheter and map-ablate catheters as well as ablation therapy catheters) are disclosed herein. In general, tip portions of catheters comprise one or more electrodes for measuring electrophysiological signals of a patient, for location sensing, or for delivering energy for therapy or stimulation (sub-therapeutic) to tissue of the patient. An impedance reduction coating above the metal surface of the electrode can reduce the impedance between the electrode and tissue contacting the electrode. The impedance reduction coating or layer can be susceptible to wear. The electrode is configured to protect the impedance reduction layer (e.g., a polymeric or other coating) from disruption of mechanical adhesion to the electrode during use, packaging, and storage in some embodiments. In some embodiments, the electrode can be partially coated with the impedance reduction layer, can be configured to protect the impedance reduction layer, and can still achieve the performance characteristics well above the performance characteristics of an uncoated electrode. In some embodiments, the electrode can be partially coated or fully coated with the impedance reduction layer, can be provided in an opening of a protective layer configured to protect the impedance reduction layer, and can still achieve the performance characteristics well above the performance characteristics of an uncoated electrode.

Figure 1:
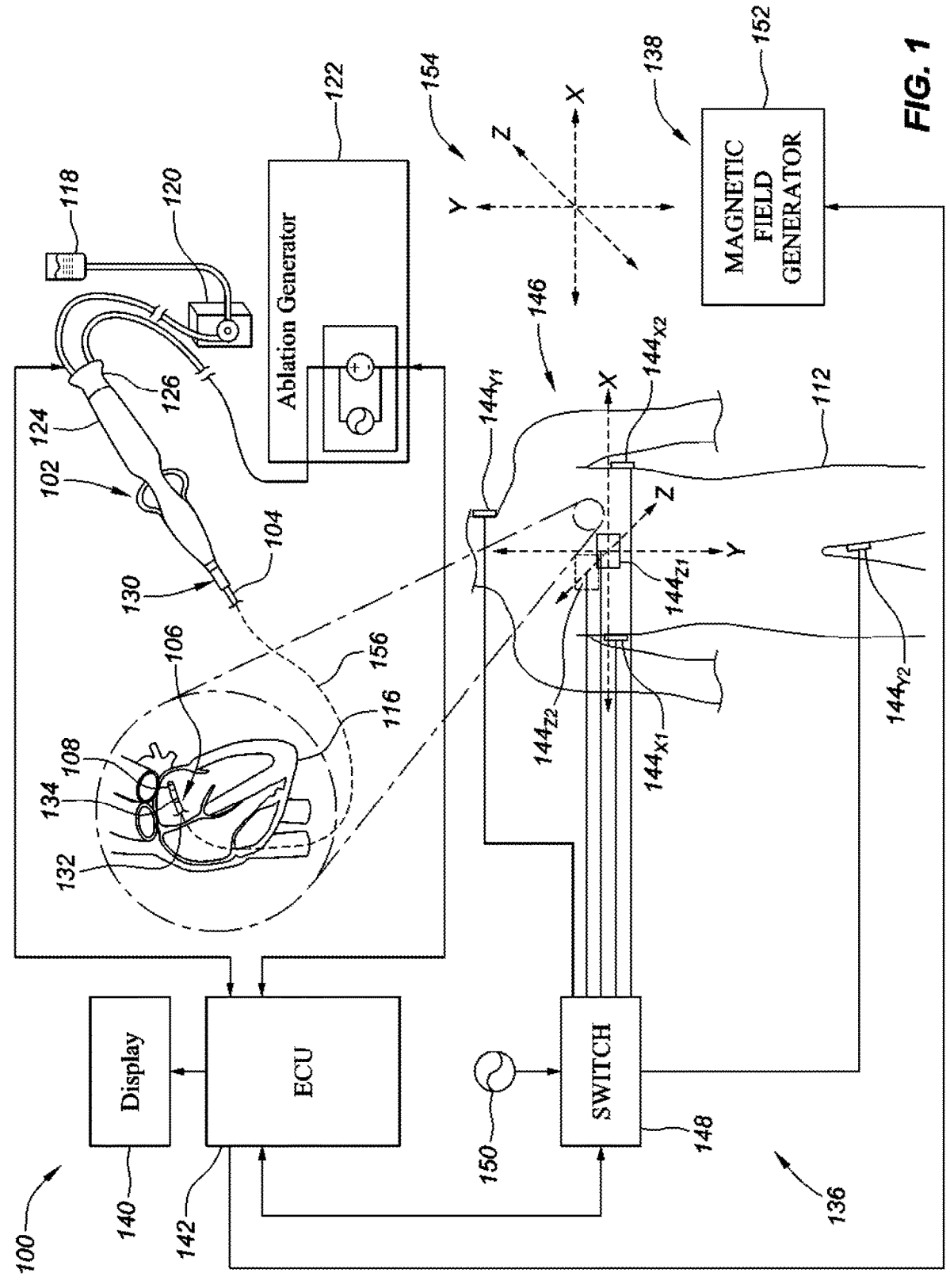
FIG. 1 is a schematic drawing of a system for navigating and operating a medical device within a body according to some embodiments.

Referring to FIG. 1, one example of a system 100 for navigating and operating a medical device within a body 112 comprises a catheter 102, such as a mapping or ablation catheter, that is shown schematically entering a heart (e.g., tissue 116) that has been exploded away from the body 112. It should be understood, however, that the system 100 can find application in connection with a wide variety of medical devices used within the body 112 for diagnosis or treatment. Further, it should be understood that the system 100 can be used to navigate medical devices used in the diagnosis or treatment of portions of the body 112 other than tissue 116 (e.g., cardiac tissue).

The catheter 102 can include a handle 124, a cable connector or interface 126 at a proximal end of the handle 124, and a shaft 104 (also referred to herein as a catheter shaft). The shaft 104 can include a proximal end 130, and a distal end 132. A tip portion 106 can be located at the distal end 132. The handle 124 provides a location for the physician to hold the catheter 102 and can further provide means for steering or guiding the shaft 104 within the body 112. For example, the handle 124 can include means to change the length of one or more pull wires extending through the catheter 102 from the handle 124 to the distal end 132 of shaft 104. The construction of the handle 124 can vary.

The shaft 104 can be made from conventional materials such as polyurethane and can define one or more lumens configured to house and/or transport electrical conductors 156, fluids, or surgical tools. The shaft 104 can be introduced into a blood vessel or other structure within the body 112 through a conventional introducer. The shaft 104 can then be steered or guided through the body 112 to a desired location such as the tissue 116 using guide wires or pull wires or other means known in the art including remote control guidance systems. The shaft 104 can also permit transport, delivery, and/or removal of fluids (including irrigation fluids and bodily fluids), medicines, and/or surgical tools or instruments. It should be noted that any number of methods can be used to introduce the shaft 104 to areas within the body 112. This can include introducers, sheaths, guide sheaths, guide members, guide wires, or other similar devices. For ease of discussion, the term introducer will be used throughout.

In some examples, the system 100 can include a positioning system, a display 140, and an electronic control unit (ECU) 142. The ECU 142 can include, but is not limited to, a central processing unit (CPU), graphics processing unit (GPU), microprocessor, application specific integrated circuit (ASIC), a field programmable gate array (FPGA), complementary metal-oxide-semiconductor (CMOS), or the like. In some examples, the ECU can include memory, such as random-access memory (RAM), read-only memory (ROM), programmable read-only memory (PROM), erasable programmable read-only memory (EPROM), and electrically erasable programmable read-only memory (EEPROM), dynamic random-access memory (DRAM), static random-access memory (SRAM), Flash memory, or the like.

The positioning system is a hybrid electric-field-based (impedance-based) and magnetic-field-based system including an electric-field-based positioning system 136 and a magnetic-field-based positioning system 138 in some embodiments. For example, the positioning system can be an EnSite Precision™ Cardiac Mapping System from Abbott Laboratories. The positioning system is provided to determine the position and orientation of the catheter 102, the tip portion 106, and similar devices within the body 112. For instance, the location or orientation of the tip portion 106 can be based on a fiducial or location of one or more electrodes of the tip portion 106, such as locational electrodes 134. In some examples, the locational electrodes 134 can include ring electrodes as shown in the example of FIG. 1. The system 136 operates based upon the principle that when low amplitude electrical signals are passed through the thorax, the body 112 acts as a voltage divider (or potentiometer or rheostat) such that the electrical potential or field strength measured at one or more electrodes, such as locational electrodes 134, on the catheter 102 can be used to determine the position of the catheter 102 relative to a pair of external patch electrodes using Ohm's law and the relative location of a reference electrode (e.g., in the coronary sinus).

In the configuration shown in FIG. 1, the electric-field-based positioning system 136 further includes three pairs of patch electrodes 144, which are provided to generate electrical signals used in determining the position of the catheter 102 within a three-dimensional coordinate system 146. The patch electrodes 144 can also be used to generate electrophysiology (EP) data (e.g., electrophysiological signals) regarding the tissue 116. To create axes-specific electric fields within body 112, the patch electrodes are placed on opposed surfaces of the body 112 (e.g., chest and back, left and right sides of the thorax, and neck and leg) and form generally orthogonal X, Y, and Z axes. A reference electrode is typically placed near the stomach and provides a reference value and acts as the origin of the coordinate system 146 for the navigation system.

In accordance with this exemplary electric-field-based positioning system 136 as depicted in FIG. 1, the patch electrodes include right side patch $144_{X1}$, left side patch $144_{X2}$, neck patch $144_{Y1}$, leg patch $144_{Y2}$, chest patch $144_{Z1}$, and back patch $144_{Z2}$; and each patch electrode is connected to a switch 148 (e.g., a multiplex switch) and a signal generator 150. The patch electrodes $144_{X1}$, $144_{X2}$ are placed along a first (X) axis; the patch electrodes $144_{Y1}$, $144_{Y2}$ are placed along a second (Y) axis, and the patch electrodes $144_{Z1}$, $144_{Z2}$ are placed along a third (Z) axis. Sinusoidal currents are driven through each pair of patch electrodes, and voltage measurements for one or more position sensors (e.g., locational electrodes 134) associated with the catheter 102 are obtained. The measured voltages are a function of the distance of the position sensors from the patch electrodes. The measured voltages are compared to the potential at the reference electrode and a position of the position sensors within the coordinate system 146 of the navigation system is determined.

The magnetic-field-based positioning system 138 in this example employs magnetic fields to detect the position and orientation of the catheter 102 within the body 112. In such a system, a magnetic field generator 152 can be employed having three orthogonally arranged coils (not shown) to create a magnetic field within the body 112 and to control the strength, orientation, and frequency of the field. The magnetic field generator 152 can be located above or below the patient (e.g., under a patient table) or in another appropriate location. Magnetic fields are generated by the coils and current or voltage measurements for one or more position sensors associated with the catheter 102 are obtained. The measured currents or voltages are proportional to the distance of the sensors from the coils, thereby allowing determination of a position of the sensors within a coordinate system 154 of system 138.

As the catheter 102 moves within the body 112, and within the electric field generated by the electric-field-based positioning system 136, the voltage readings from the locational electrodes 134 change, thereby indicating the location of catheter 102 within the electric field and within the coordinate system 146 established by the system 136. The locational electrodes 134 can be adapted to communicate position signals to the ECU 142.

The catheter 102 can be configured to deliver treatment as well as geometric modeling or electrophysiological mapping. In some examples, the catheter 102 can include at least one electrode 108 configured to detect electrophysiological signals from the tissue 116 or to provide energy for ablating the tissue 116. In an example, the at least one electrode 108 can be communicatively coupled to the ablation generator 122 for delivery of electrical signals adapted to provide the ablation energy to the at least one electrode 108. The ablation generator 122 can be an Ampere™ Generator from Abbott Laboratories and provides a sinusoidal electrical signal at 485 kilohertz (kHz) in some embodiments. Other types, frequencies, and forms of RF signals can be provided from the ablation generator 122. In some embodiments, at least one electrode 108 is an electrode assembly that may be used for a variety of diagnostic and therapeutic purposes including, for example and without limitation, cardiac mapping and/or ablation (e.g., RF ablation or Irreversible Electroporation (IRE ablation)/Pulsed Field Ablation (PFA)). The ablation generator 122 can be configured for PFA In some embodiments, the tip portion 106 includes tip electrodes associated with a grid catheter or basket catheter such as those discussed below with reference to FIGS. 2A-B. The electrodes 108 and 134 can include an impedance reduction coating or layer to reduce the impedance of the electrodes, generally, and, in some examples, to mitigate the increased impedance of the reduced-size electrodes. The electrodes 108 and 134 can be partially coated (e.g., 8 or more percent, 25 or more percent, etc.) with the impedance reduction layer disposed in a recess in the electrodes 108 and 134. Partially coating the electrodes 108 and 134 with the impedance reduction layer achieves similar performance and allows the electrodes 108 and 134 to be configured to protect the impedance reduction layer in some embodiments. The recess protects the impedance reduction layer from wear by native material of the electrodes 108 and 134 as explained in more detail with respect to the embodiments of electrodes discussed herein.

In some embodiments, electrodes 108 and 134 include platinum iridium native material partially coated with an impedance reduction layer (e.g., polymer-based impedance reduction layer). The native material can also be gold, platinum, or other conductive materials. The impedance reduction layer allows the electrodes 108 and 134 to have lower impedance across all frequencies and to have a wider current versus voltage response, thereby providing better electron flow.

By plating or coating electrodes 108 used for ablation with the impedance reduction layer, energy is delivered more efficiently, thereby capturing more tissue with less energy (e.g., reduced by at least 5 times). Making current/power delivery more effective at a lower energy in ablation procedures potentially resolves undesired muscle and nerve stimulations in some embodiments. By plating or coating electrodes 108 used for mapping with the impedance reduction layer, better performance is achieved due to the lower impedance (e.g., signal to noise improvement, lower amplification requirements, lower filtering requirements, etc.) in some embodiments. By plating or coating electrodes 108 used for high density mapping and ablation, focal identification of arrhythmia source or anatomical paths of activation (or origination locations) is achieved as well as ablation of the smallest effective area of tissue in some embodiments.

In some examples, the catheter 102 can be optionally connected to a fluid source 118 for delivering a biocompatible irrigation fluid such as saline through a pump 120. The pump 120 can include a fixed rate roller pump or variable volume syringe pump with a gravity feed supply from fluid source 118 as shown. The connector or interface 126 provides mechanical, fluid, and electrical connections for conduits or cables extending from the pump 120 and the ablation generator 122. The catheter 102 can also include other conventional components not illustrated herein such as a temperature sensor, additional electrodes, and corresponding conductors or leads.

The ECU 142 provides a device for controlling and monitoring the operation of various components of the system 100, including the catheter 102, the ablation generator 122, and the hybrid positioning system. The ECU 142 can also provide a device for determining electrophysiology characteristics (e.g., signals) of the tissue 116, the position and orientation of the catheter 102 relative to tissue 116 and the body 112, controlling the ablation of the tissue 116, or any combination thereof. The ECU 142 also provides a device for generating display signals used to control the display 140.

The display 140 is provided to convey information to a physician to assist in diagnosis and treatment. The display 140 can comprise one or more conventional computer monitors or other display devices. The display 140 can present a graphical user interface (GUI) to the physician. The GUI can include a variety of information including, for example, an image of the geometry of the tissue 116, electrophysiology data (e.g., maps of signals from the electrode 108) associated with the tissue 116, graphs illustrating voltage levels over time for various locational electrodes 134, and images of the catheter 102 and other medical devices and related information indicative of the position of the catheter 102 and other devices relative to the tissue 116.

Figure 2A:
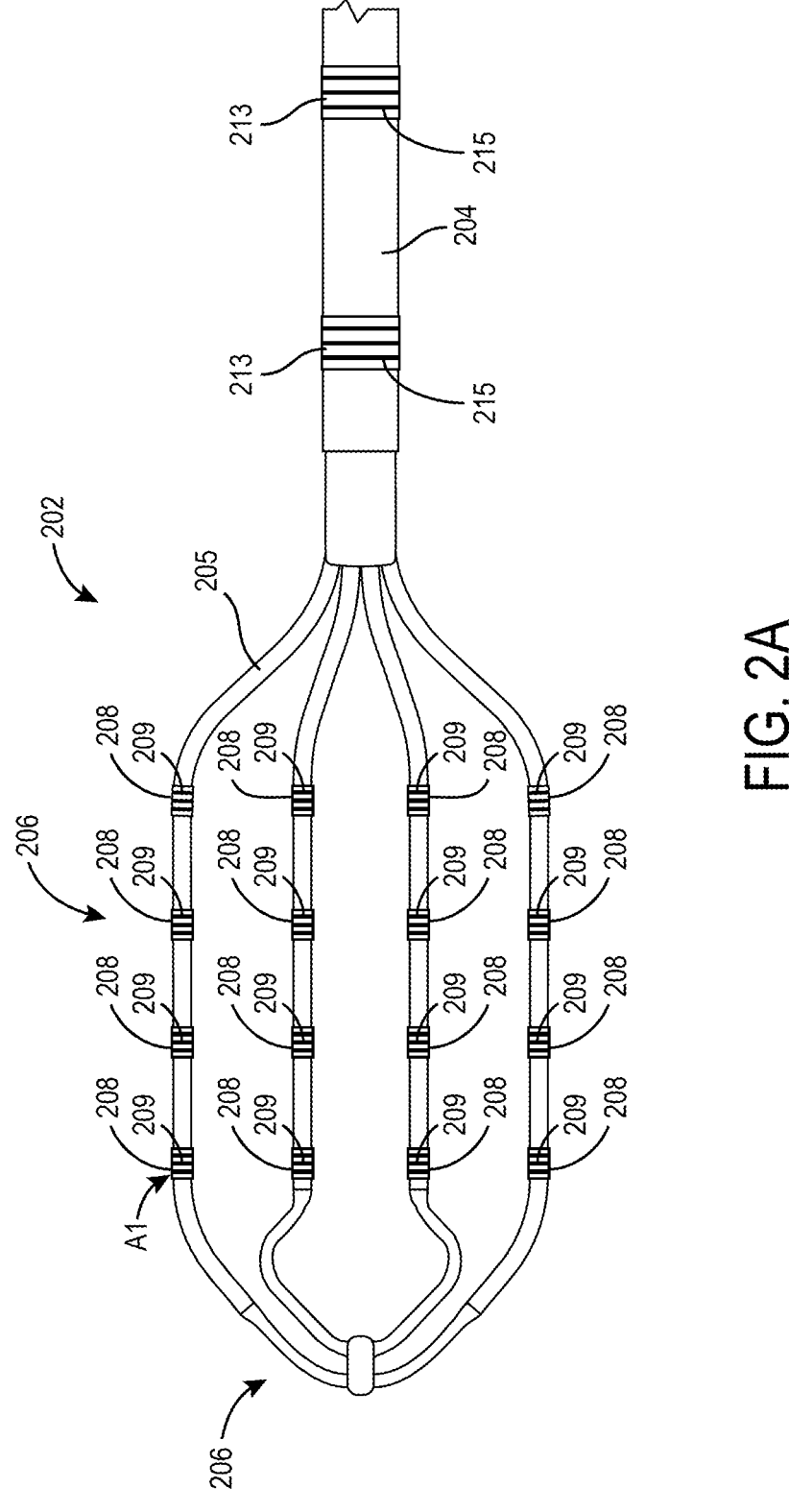
FIG. 2A is a top view schematic drawing of one or more electrodes along at least one arm of a catheter according to some embodiments.
Figure 2B:
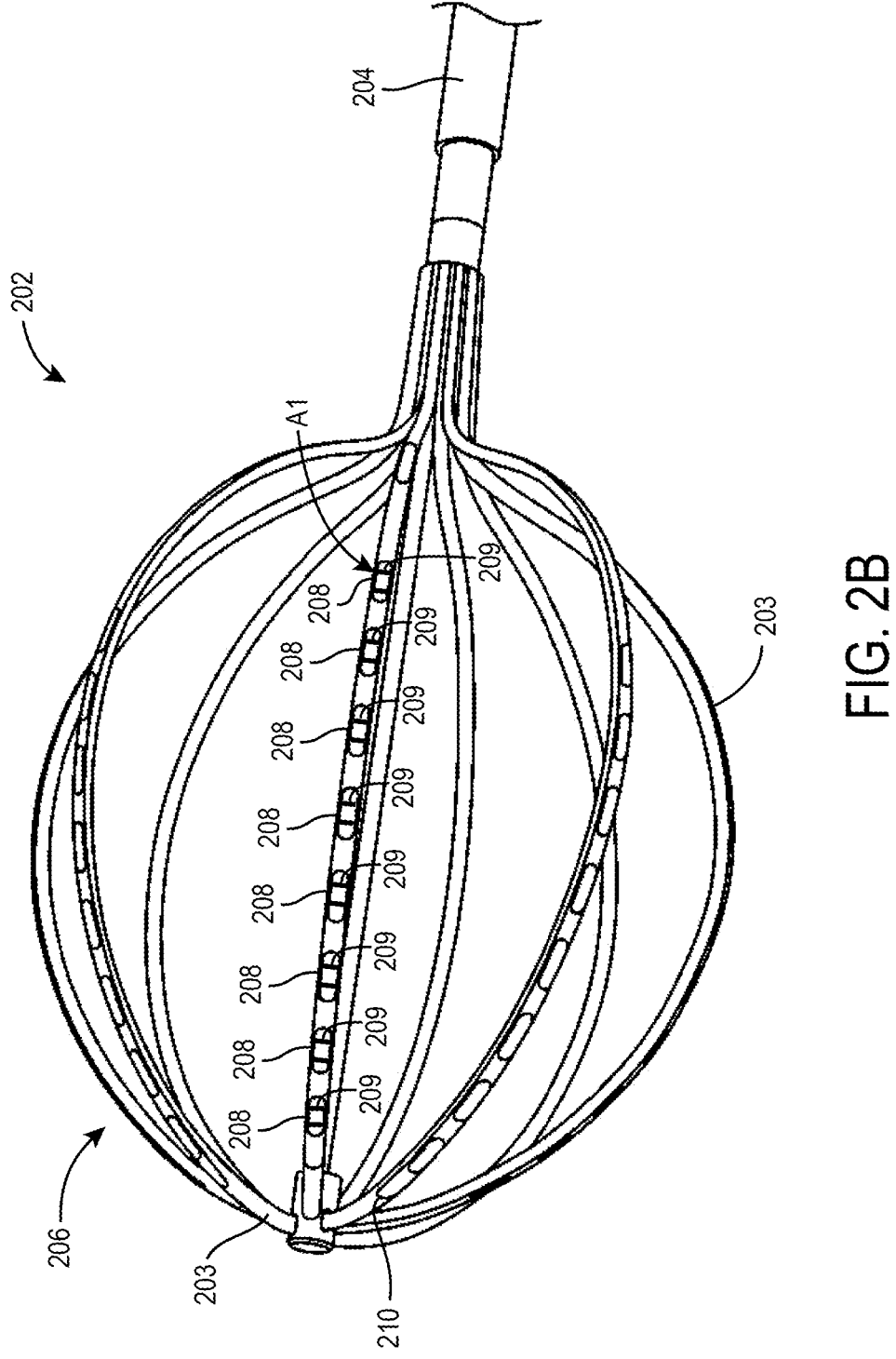
FIG. 2B is a perspective view schematic drawing of one or more electrodes along at least one spline of a basket catheter according to some embodiments

With reference to FIG. 2A, a catheter 202 includes a tip portion 206, such as a tip portion of the Advisor™ HD Grid Mapping Catheter, Sensor Enabled™ device from Abbott Laboratories. The tip portion 206 includes one or more electrodes 208 along at least one arm 205. The tip portion 206 can have a planar configuration in some embodiments. In some embodiments, the tip portion 206 is configured as a basket catheter with electrodes 208 disposed on at least one spline 203 as shown in FIG. 2B. Although catheter 202 is discussed as used in mapping procedures, electrodes 208 can be used in any type of medical procedure and are not limited to use in mapping procedures. The number of electrodes 208 can vary for example 1, 2, 4, 8, 16, 32, 48, 128, etc. and be provided in a variety of matrix layouts or patterns.

In the examples of FIGS. 2A and 2B, the catheter 202 can be a mapping catheter that can be used to map electrophysiological signals within the heart of a patient, as previously described in FIG. 1. In various examples, the catheter 202 can be a mapping catheter, ablation catheter, a dual functionality mapping/ablation catheter, or other type of catheter. In the examples of FIGS. 2A and 2B, the catheter 202 can include a number of electrodes 208 in a distributed pattern along each arm 205 (FIG. 2A) or spline 203 (FIG. 2B). In some examples, increasing the density of the electrodes 208 can provide for an increased number of electrodes 208 along the catheter 202 (e.g. the tip portion 206 of the catheter 202) and an increased resolution of the measurement of the electrophysiological signals within (and accordingly an electrophysiological map) of the tissue, or a combination thereof. The density of the electrodes 208 can be increased by decreasing the spacing of the electrodes 208, decreasing a contact surface area A1 of the electrodes 208, or both. Where the contact surface area A1 of the electrodes 208 is decreased, the impedance between tissue and the electrodes 208 that are in contact with the tissue can increase accordingly. For instance, the impedance of the electrophysiological signal can include a resistance component and a reactance component. The resistance component and the reactance component can increase corresponding to the decrease in the contact surface area A1 of the electrodes 208.

In another example, the reactance component can increase at a greater rate than the resistance component as the frequency of the electrophysiological signal decreases. In further example, the reactance component can increase at a greater rate than the resistance component as the contact surface area A1 decreases. Accordingly, the reactance component can increase corresponding to the decrease in the contact surface area A1, a decrease of the frequency of the electrophysiological signal, or a combination thereof. The electrodes 208 can be small-scale electrodes. As discussed herein, small-scale electrodes can include a contact surface area A1 of less than one square millimeter. In some embodiments, the electrodes 208 are larger than small scale electrodes. In some embodiments, the electrodes 208 have a contact surface area of greater than 1 square millimeter (e.g., 1, 2, 2.5, 5, etc. square millimeters).

The electrodes 208 can include an impedance reduction layer 209 to reduce the impedance of the electrodes 208, generally, and, in some examples, to mitigate the increased impedance of the reduced-size electrodes 208. In an example, the resistance component, the reactance component, or both components of the electrodes 208 can be reduced by including the impedance reduction layer 209 on the electrodes 208. In another example, across a range of frequencies (e.g., 1 to 20,000 Hz) the resistance component, the reactance component, or combinations thereof can be reduced by inclusion of the impedance reduction layer 209. The impedance reduction layer 209 can be used to reduce the impedance of the electrodes, generally, and in some examples, to mitigate the increased impedance of the reduced-size electrodes. Reducing the impedance at the electrodes 208 can provide for increased fidelity of the electrophysiological signal measurement. In some embodiments, all of the electrodes 208 are partially covered by the impedance reduction layer 209 while in other embodiments fewer than all of the electrodes 208 are partially covered the impedance reduction layer 209. In some embodiments, the electrodes 208 that are disposed in positions more prone to wear are partially coated with the impedance reduction layer 209 while electrodes 208 in positions less prone to wear are fully coated with the impedance reduction layer 209. In some embodiments, the electrodes 208 are coupled to a wire that is connected to the ECU 142 and/or the ablation generator 122.

In some examples, the one or more electrodes 208 can be located on a flexible circuit 210 (FIG. 2B). The flexible circuit 210 can be attached to a shaft 204 of the catheter 202 and spline 203. For instance, the flexible circuit 210 can include a complementary shape to conform the flexible circuit 210 to the geometry of the shaft 204 or spline 203. In some embodiments, the spline 203 includes a tube to which the flexible circuit 210 is attached. The electrodes 208 have various sized and shaped areas and configuration as well as various thicknesses depending upon design criteria. In some embodiments, the electrodes 208 can be oval, square, rectangular, diamond shaped, hexagonal, or round flat planar electrodes. The electrodes 208 can be relatively flat or have a three dimensional shape in some embodiments. In some embodiments, the electrodes 208 can be ring shaped electrodes that surround spline 203 or arm 205. In some embodiments, the electrodes 208 are C-shaped and partially surround the spline 203 or arm 205. In some embodiments, the electrodes 208 are ring shaped platinum/iridium metal structures partially coated with the impedance reduction layer 209 (e.g., intrinsically conducting polymers (ICPs) that increase the charge injection capability and lower the impedance of the electrodes 208).

In some embodiments, the surface of one or more of the electrodes 208 is patterned or configured to have one or more recessed portions, and the impedance reduction layer 209 is disposed in the one or more recessed portions. The impedance reduction layer 209 is disposed so that the native electrode surface (e.g., the metal surface) projects above the impedance reduction layer 209 and protects the impedance reduction layer 209 from potentially abrasive loads (e.g., due to insertion, withdrawal, valves, sheath tips, etc.). In some embodiments, laser patterns, lithographically etched patterns, micro-machined patterns, additive manufacturing patterns, deposition-based (e.g., vapor deposition, cold spray, etc.) patterns, or impression-based (e.g., stamping, coining, knurling, etc.) patterns are created in the surface of the electrodes 208 and the impedance reduction layer 209 is contained in the recessed portions (e.g. crevices) associated with the patterns, thereby protecting the impedance reduction layer 209. In some embodiments, larger aspect features (e.g., a raised edge around a pocket) are used to protect the coating. The larger aspect features are constructed by plating/masking steps, additive manufacturing steps, and/or during the metallization used to create the electrodes 208 in some embodiments. In some embodiments, the impedance reduction layer 209 has a thickness that is less than the depth of the recessed portions or the larger aspect features.

In the example of FIG. 2A, electrodes 214 are disposed on the shaft 204. The surface of the electrodes 214 are patterned or configured to have one or more recessed portions, and an impedance reduction layer 215 is disposed in the one or more recessed portions similar to the electrodes 208 discussed above. Electrodes 214 are ring electrodes attached to wires in some embodiments.

Figure 2C:
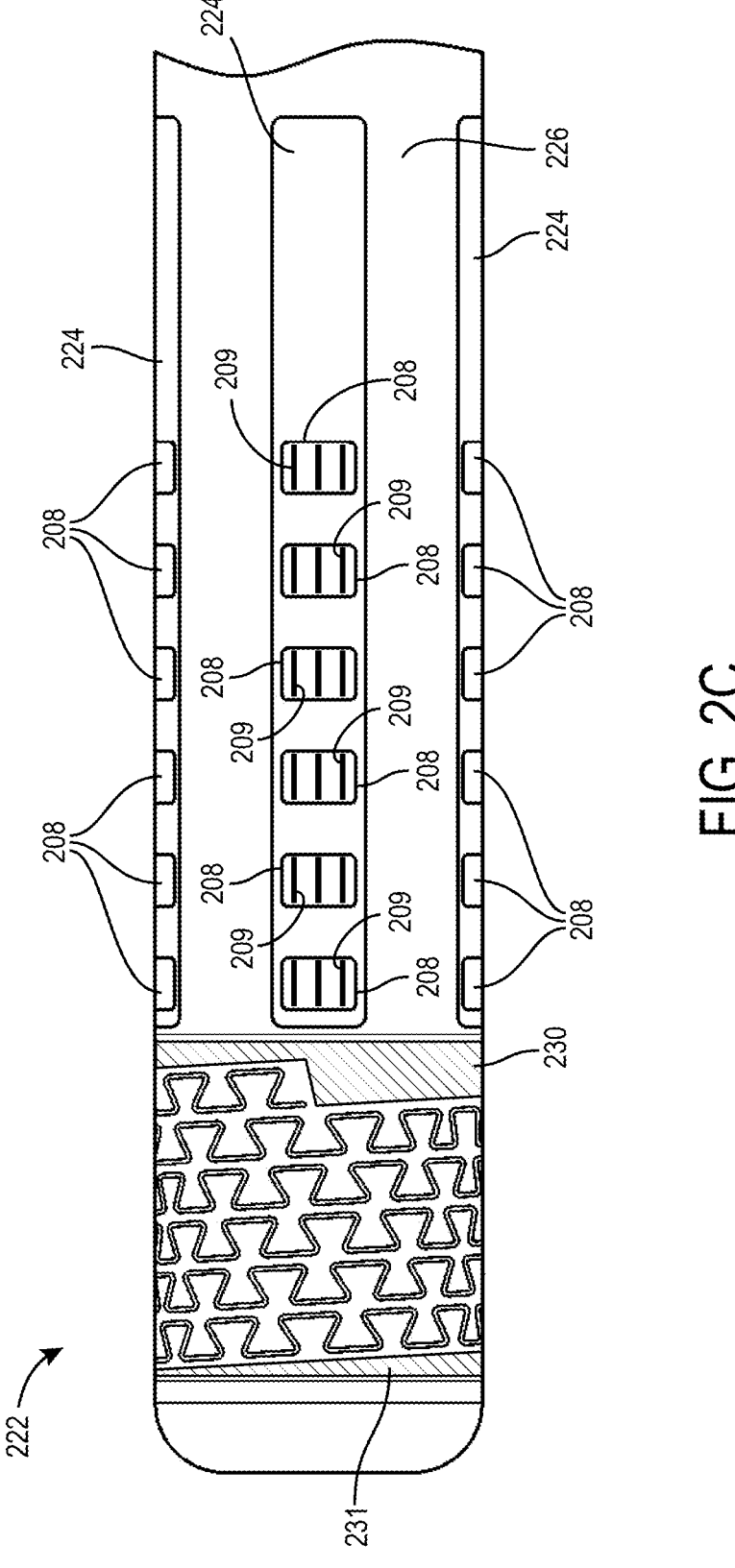
FIG. 2C is a side view schematic drawing of an ablation catheter according to some embodiments.

With reference to FIG. 2C, an ablation catheter 222 includes one or more flexible circuits 224 fixedly attached to the shaft 226 of the catheter 222. For example, the flexible circuits 224 can be attached to the shaft 226 using an adhesive. In the example of FIG. 2C, the catheter 1002 can include four flexible circuits 224. The flexible circuits 224 can be arranged at 90 degrees radially from one another along an outer diameter of the shaft 226. The flexible circuits 224 can include a number of electrodes 228 spaced thereon. The electrodes 228 can include an impedance reduction layer 229 as described further herein. In a further example, the flexible circuits 224 can include an intermediate layer as described below. The catheter 222 can include an ablation electrode 230 at the distal end of the shaft 226. The ablation electrode 230 can include an impedance reduction layer 231. In some embodiments, the surface of one or more of the electrodes 228 and the electrode 230 is patterned or configured to have one or more recessed portions, and the impedance reduction layers 229 and 231 are disposed in the one or more recessed portions. Accordingly, impedance reduction layers 229 and 231 of the ablation electrode 230 and the electrodes 228 are protected from wear. The ablation electrode 230 can provide ablation therapy to the tissue, and the electrodes 228 can be used to measure electrophysiological signals within the tissue for diagnosis, mapping, or identification of an ablation site.

Figure 3:
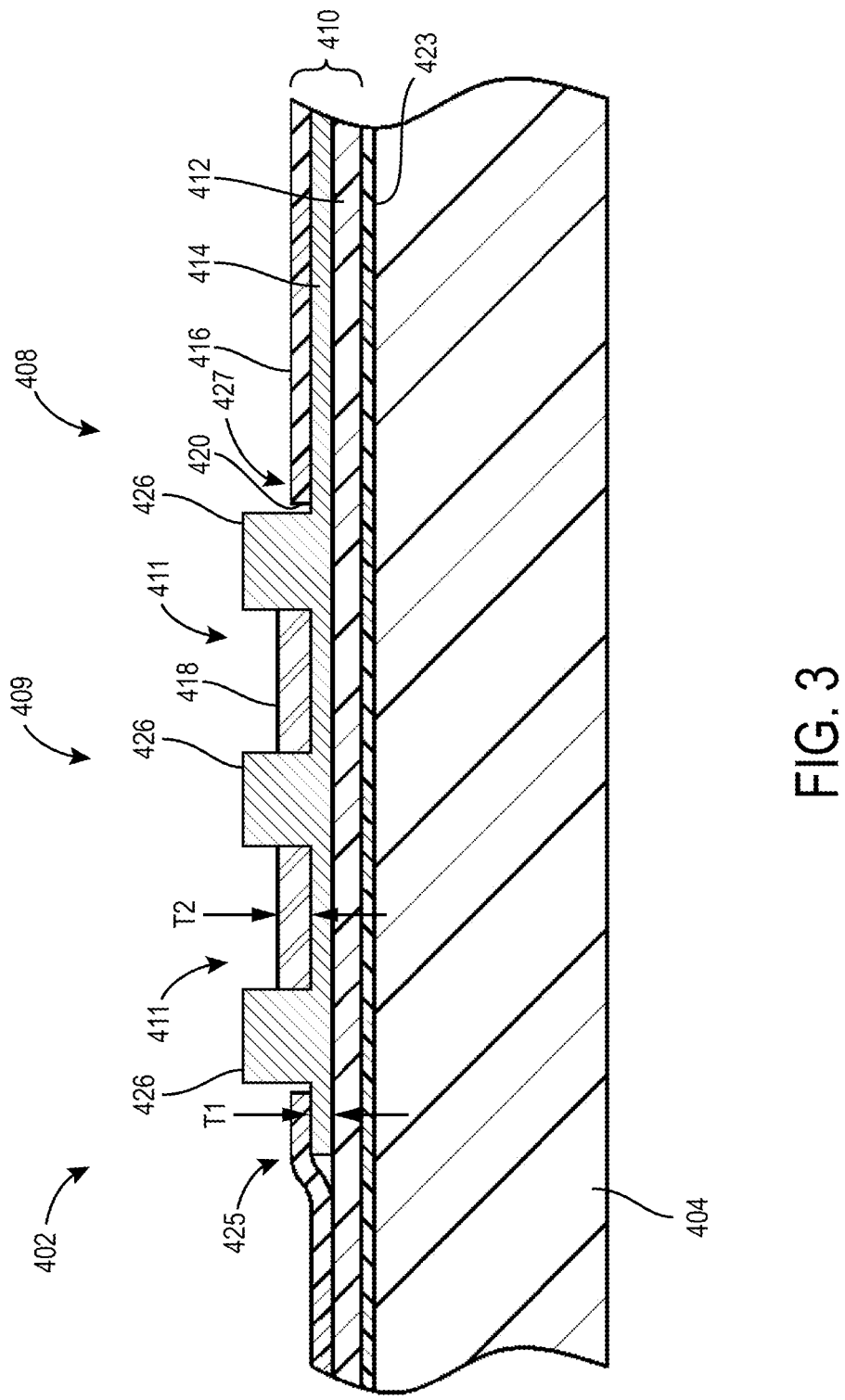
FIG. 3 is a cross sectional view schematic drawing of a catheter including at least one electrode with an impedance reduction layer according to some embodiments.

With reference to FIG. 3, a catheter 402 include at least one electrode 408 disposed thereon. In the example of FIG. 3, the electrode 408 includes an impedance reduction layer 418 at a contact surface area 409. As depicted, the electrode 408 can be included in a flexible circuit 410. The flexible circuit 410 can be attached to a substrate 404 of the catheter 402, such as the arm 205, the spline 203 or the shaft 204 and 226 (as shown in the examples of FIGS. 2A, 2B, and 2C). In an example, an adhesive 423 can be located between the dielectric layer 412 and the substrate 404 to attach the flexible circuit 410 to the substrate 404. The flexible circuit 410 can be a single conductive layer flexible circuit as shown in the example of FIG. 3 or a flexible circuit with multiple conductive layers. The electrode 408 extends from an end 425 to an end 427. The flexible circuit 410 can house additional electrodes similar to electrode 408.

In the example FIG. 3, the flexible circuit 410 can include a first dielectric layer 412, an electrical conductor 414, a second dielectric layer 416, and the electrode 408 including the impedance reduction layer 418. The dielectric layer, such as the dielectric layer 412 or the dielectric layer 416, can include an electrically insulating polymer, for example polyimide, polyester, polyethylene terephthalate, polyethylene naphthalate, polyetherimide, various fluoropolymers, copolymers, or other suitable flexible substrate. An electrically conductive layer can be disposed on the first dielectric layer 412 to form the electrical conductor 414. The electrical conductor 414 can be constructed from a material including, but not limited to, copper, copper nickel alloy, nitinol, inconel, silver filled epoxy, carbon, aluminum, gold, silver, platinum, alloys thereof, or the like. In various examples, the electrical conductor 414 can be a metallic film that is applied to the first dielectric layer 412 with an adhesive, or the electrical conductor 414 can be electrodeposited on to the dielectric layer 412. In an example, the metal film can be etched to form the electrical conductor 414, for example to form the geometry of the electrical traces for routing electrical signals between the electrode 408 and the ECU 142 and to define the contact surface area 409. The electrical conductor 414 can have a thickness T1 between 10 microns and 125 microns or between 25 microns and 125 microns (inclusively) and can be multiple layers. The contact surface area 409 is an area where the electrode 408 can make contact to the body 112 and includes the exposed portion of the electric conductor 414 within the aperture in dielectric layer 416 and impedance reduction layer 418 in some embodiments.

In a further example, the electrical conductor 414 can be directly attached to the substrate 404 of the catheter 402, such as an arm (e.g., arm 205), a spline (e.g., spline 203), a shaft (e.g., shaft 104), or tip portion (e.g., tip portion 206) of the catheter 402. In an example, the electrical conductor 414 can be a metallic film that is applied to the substrate 404 with an adhesive. In various other examples, the electrical conductor 414 can be applied to the substrate 404 using electrodeposition, aerosol jet, vapor deposition, chemical deposition, or the like.

The impedance reduction layer 418 can be disposed on the electrical conductor 414. The impedance reduction layer 418 can reduce impedance between the tissue and the electrical conductor 414. In some examples, the impedance reduction layer 418 can have a surface texture or can be combined with a surface texture configured to reduce the impedance between the tissue and the electrode 408. The impedance reduction layer 418 can be disposed on the electrical conductor 414, for instance, by one or more techniques including, but not limited to, electrodeposition, vapor deposition, chemical deposition, aerosol jet, application of a foil, or other type method of applying the impedance reduction layer 418. The impedance reduction layer 418 can include a thickness T2 between 1 μm and 30 μm, preferably between 1 μm and 5 μm (inclusively). In a further example, the electrical conductor 414 can be directly attached to the substrate 404 of the catheter 402, such as a spline (e.g., spline 203 in FIG. 2B), arm (e.g., arm 205 in FIG. 2A), a shaft (e.g., shaft 104 in FIG. 1), or tip portion (e.g., tip portion 206) of the catheter 402. Materials for the impedance reduction layer 418 are discussed below.

Figure 4:
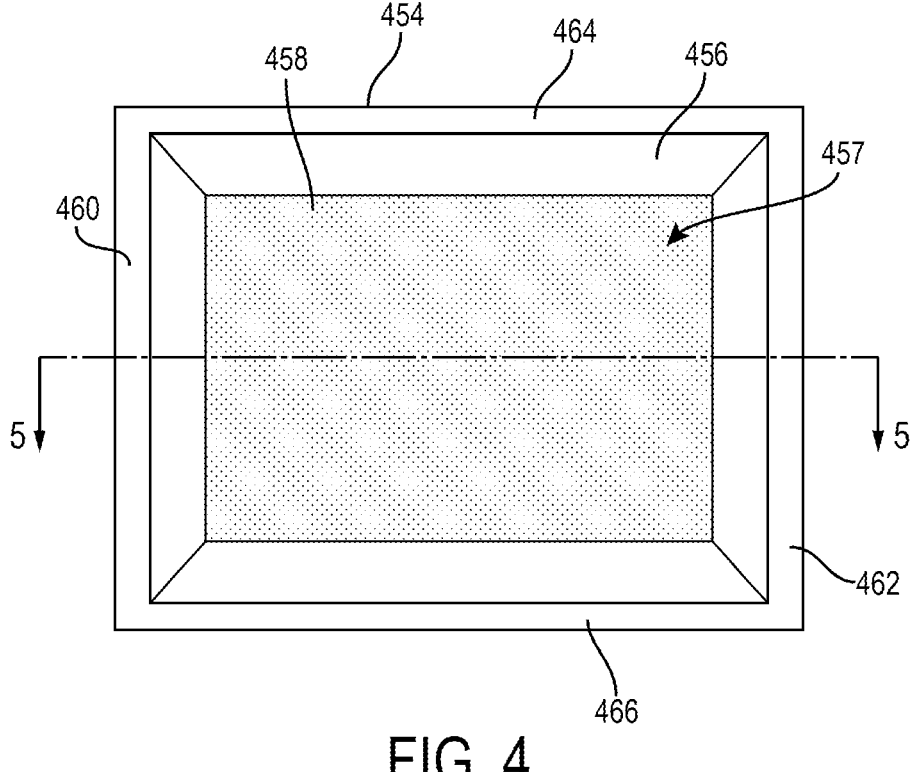
FIG. 4 is a top view planar schematic drawing of an electrode for use on a catheter according to some embodiments.

The second dielectric layer 416 can be disposed over the electrical conductor 414 to electrically insulate and protect the electrical conductor 414. The second dielectric layer 416 can include one or more apertures 420 to expose the electrode 408 to provide the contact surface area 409 for placement against tissue within the body. In some examples, the aperture 420 can be constructed by laser cutting, punching, etching, or the like. In the example of FIG. 4, the contact surface area 409 of the electrode 408 can be extended through the aperture 420. In other examples, the second dielectric layer 416 can be disposed over a portion of the electrode 408 (e.g., the impedance reduction layer 418) as well as the electrical conductor 414. Accordingly, the second dielectric layer 416 can increase the attachment strength of the electrode 408 to the flexible circuit 410, such as to the electrical conductor 414, first dielectric layer 412, or a combination thereof. The first dielectric layer 412, the second dielectric layer 416, or both can include a thickness of between 25 μm to 125 μm, preferably between 25 μm and 50 μm (inclusively).

In some embodiments, the electrical conductor 414 is one or more layers configured to have portions 426 that extend above the top surface of the impedance reduction layer 418 at the location of the contact surface area 409. The portions 426 can be formed by any technique including but not limited to patterning, plating, or selective deposition. In some embodiments, a metal layer is deposited above the electrical conductor 414 in the contact surface area 409. The deposited metal layer is masked and etched to leave the portions 426, or the portions 426 are selectively grown on the electrical conductor 414. In some embodiments, the impedance reduction layer 418 is formed after portions 426 are formed. The impedance reduction layer 418 is two or more layers in some embodiments. In some embodiments, an intermediate layer can be disposed between the electrical conductor 414 and the impedance reduction layer 418. In an example, the intermediate layer can include a material that is compatible with the material of the electrical conductor 414 and the impedance reduction layer 418. For instance, the intermediate layer can facilitate adhesion between the electrical conductor 414 and the impedance reduction layer 418. In an example, the intermediate layer can include gold or a gold alloy and portions 426 can be formed of the intermediate layer. Portions 426 can be coated with conductive material, such as gold, platinum, etc. Electrode 408 can be formed in an additive manufacturing process.

Portions 426 extend above a top surface of the impedance reduction layer 418 and provide wear protection for the impedance reduction layer 418 in some embodiments. In some embodiments, portions 426 extend less than 5 microns (e.g., 1-2 microns) above a top surface of impedance reduction layer 418 so that portions 426 do not unduly interfere with the contact between the impedance reduction layer 418 and the tissue 116 (FIG. 1). In some embodiments, the portions 426 are ridges, cylinders, or other structures that define recessed portions 411 for the contact surface area 409. The recessed portions 411 can be provided in any a pattern. For example, the recessed portions 411 can be in a checkerboard pattern, circular pattern, linear pattern, a concentric pattern, etc.

Figure 5:
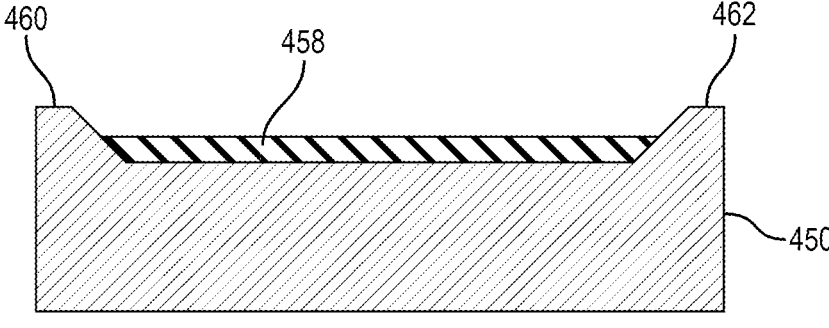
FIG. 5 is a cross sectional view schematic drawing of the electrode illustrated in FIG. 4 about line 5-5 according to some embodiments.

With reference to FIGS. 4 and 5, an electrode 454 can be used in a catheter, such as attached at a distal end 132 of catheter 102 (FIG. 1). Electrode 454 is rectangular or square shaped in some embodiments. In some embodiments, the main surface area of electrode 454 is round, pentagonal, octagonal, diamond shaped, circular, oval, or any appropriate shape. The pattern of electrode 454 can be repeated on other electrodes or on the same electrode in some embodiments. In some embodiments, electrode 454 is prismatic, cylindrical, or relatively flat.

In some embodiments, the electrode 454 includes a conductive layer 450 with a recess 457 and an impedance reduction layer 458. Materials associated with the electrical conductor 414 (FIG. 3) can be used as materials for the conductive layer 450. In some embodiments, the conductive layer 450 is integrated with or part of a conductor connected to the ECU 142 (FIG. 1). Edges 460, 462, 464 and 466 at the perimeter of the electrode 454 define the recess 457 for the impedance reduction layer 458. The conductive layer 450 includes one or more layers of robust material (e.g., metal such as, platinum/iridium) as compared to the material for impedance reduction layer 458 (e.g., a polymer-based material). In some embodiments, a top layer of the conductive layer 450 has better wear characteristics than a lower layer or has better compatibility with tissue than the lower layer. The edges 460, 462, 464 and 466 project above the impedance reduction layer 458 and protect the impedance reduction layer 458 from abrasive loads seen by the electrode 454 in some embodiments. For example, the edges 460, 462, 464 and 466 extend high enough from impedance reduction layer 458 to protect impedance reduction layer 458 from wear. The edges 460, 462, 464 and 466 can have slanted or perpendicular walls. The difference in height between the edges 460, 462, 464 and 466 and a top surface of the impedance reduction layer 458 can vary depending upon design parameters. In some embodiments, the difference is between 1 and 20 microns. In some embodiments, the difference is approximately 2-8 (e.g., 3 microns) microns. The impedance reduction layer 458 is the same material as impedance reduction layer 418 in some embodiments.

In some examples, the impedance reduction layer 458 is a compliant, conformal material. The impedance reduction layer 458 as well as other impedance reduction layers discussed herein can include, but are not limited to, a conductive stretchable polymer, a printable conductive polymer, a conductive stretchable ink, iridium oxide, indium tin oxide (ITO), single-wall carbon nanotubes, multi-wall carbon nanotubes, carbon nanotube ribbons, carbon nanotube aerogel, poly[styrene-b-(ethylene-co-butylene)-b-styrene triblock copolymer compounded with single-wall or multi-wall carbon nanotubes, polyaniline (PANI) covalently bonded to poly(styrene-co-ethylenebutylene-co-styrene, poly(3,4-ethylenedioxythiophene):poly(styrenesulfonate) (PEDOT:PSS), poly(3,4-ethylenedioxythiophene):p-tosylate (PEDOT), polyacrylic acid (PAA) implanted gold (Au) or titanium (Ti) or palladium (Pd) ions, copper (e.g., copper nanoparticles), gold (e.g., gold nanoparticles), silver (e.g., silver nanoparticles), zinc (e.g., zinc nanoparticles), spherical citrate stabilized Au nanoparticles, Au nanowires, gallium arsenide (GaAs) nanoribbons, silicon (Si) nanoribbons, silicon nanowires, graphene and silver nanowire hybrid foam, or the like. Where impedance reduction layer 458 includes a rigid material, such as gold, titanium, palladium, copper, silver, zinc, or the like, the conductive layer 450 can be combined with a more compliant material to form a composite material. In another example, the impedance reduction layer 458 can include at least one strain relief feature to increase the extensibility and compliance of the conductive material to form the compliant conductive material. In some embodiments, impedance reduction layer 458 is a PEDOT-based conductive polymer coating including a PDOT molecule combined with a strong polyelectrolyte (PSS) anion and another anion.

In some embodiments, the impedance reduction layer 458 covers between 90 percent and 8 percent of the exposed surface area or contact surface area of the electrode 454. The contact surface area of the electrode 454 is an area where the electrode 454 can electrically make contact to the body 112 and includes the area of the impedance reduction layer 458 and the conductive layer 450 that are exposed for contact to the body 112 (FIG. 1) in some embodiments. In some embodiments, the impedance reduction layer 458 covers between 75 percent and 12 percent of the contact surface area of the electrode 454 of the electrode 454. In some embodiments, the impedance reduction layer 458 covers between 60 percent and 8 percent of the contact surface area of the electrode 454 of the electrode 454. In some embodiments, the impedance reduction layer 458 covers approximately 44 percent of the exposed surface area of the electrode 454.

Figure 6:
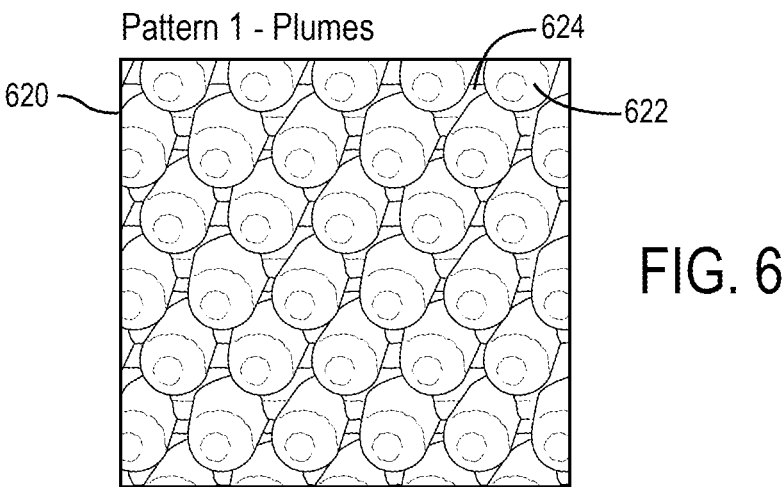
FIG. 6 is a perspective view schematic drawing of an electrode surface pattern on an electrode for a catheter according to some embodiments.

With reference to FIG. 6, the contact surface area, such as contact surface area 409 (FIG. 4) or a surface are of a ring electrode can be provided with a pattern 620 as represented on a scanning electron microscope scan. After a conductive layer (e.g., a metal layer) is provided on a substrate or otherwise formed, the conductive layer is subjected laser patterning to provide an electrode surface with recessed portions that protect the polymer coating contained therein. The pattern 620 includes cylindrical plumes 622 that define the crevices or recessed portions 624 of the conductive layer. The pattern 620 can include plumes 622 having a height including, but not limited to 1 to 30 μm. The recessed portions 624 have a depth of approximately 20 microns, and the plumes 622 are spaced 25 microns from each other in some embodiments. The impedance reduction layer (similar to impedance reduction layers 418 (FIG. 3) and 458 (FIG. 4)) can be provided in the recessed portions 624 by dipping followed by a chemical mechanical polish to remove the impedance reduction layer 418 from the top surface of the plumes 622. Other deposition processes can be used to provide the impedance reduction layer. The pattern 720 can be more coarse or fine depending on design considerations, and the density of plumes 622 can be varied depending on design parameters, such as level of abrasion protection and amount of impedance reduction.

Figure 7:
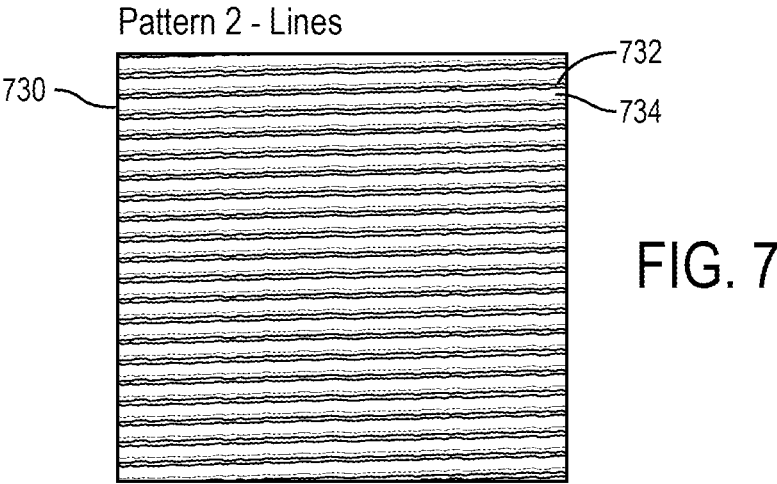
FIG. 7 is a perspective view schematic drawing of an electrode surface pattern on an electrode for a catheter according to some embodiments.

With reference to FIG. 7, the contact surface area, such as contact surface area 409 (FIG. 4) can be provided with a pattern 730 as represented on a scanning electron microscope scan. After a conductive layer (e.g., a metal layer) is provided on a substrate or otherwise formed, the conductive layer is subjected laser patterning to provide an electrode surface according to the pattern 730 similar to the pattern 620. The pattern 730 includes ridges 732 that define the troughs, valleys or recessed portions 734 of the conductive layer. The ridges are 15-30 microns apart and the recessed portions 734 are 1 to 30 microns deep in some embodiments. The impedance reduction layer can be provided in the recessed portions 734 by dipping followed by a chemical mechanical polish to remove the impedance reduction layer from the top surface of the ridges 732.

Figure 8:
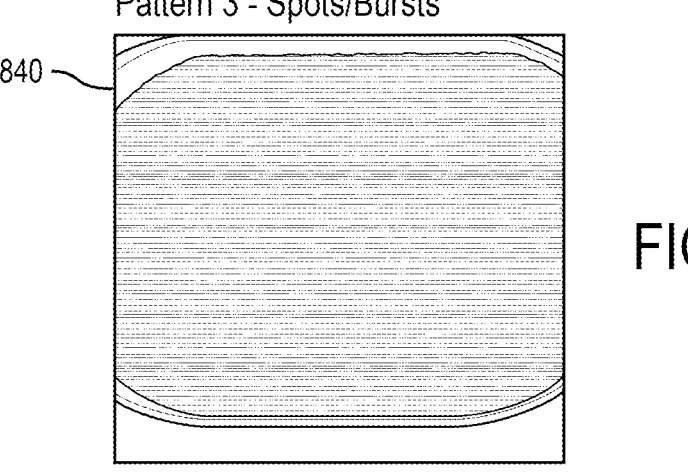
FIG. 8 is a perspective view schematic drawing of an electrode surface pattern on an electrode for a catheter according to some embodiments.

With reference to FIG. 8, the contact surface area, such as contact surface area 409 (FIG. 4) can be provided with a pattern 840 as represented on a scanning electron microscope scan. After a conductive layer (e.g., a metal layer) is provided on a substrate or otherwise formed, the conductive layer is subjected laser patterning to provide an electrode surface according to a pattern 840 similar to the pattern 620. The pattern 840 is a spotted pattern that defines recessed portions of the conductive layer. The impedance reduction layer can be provided in the recessed portions by dipping followed by a chemical mechanical polish.

The patterns 620, 730, and 840 are exemplary only. Other patterns or textures can be utilized. For example, a circular concentric ridge pattern, a rectangular pattern, or oval pattern can be provided. The patterns 620, 730, and 840 can be adjusted to provide a particular percentage of coverage of the impedance reduction layer and level of protection. For example, the density of ridges and valleys can be adjusted for design considerations. Larger or smaller ridges and recessed portions can be provided depending upon design considerations, such as impedance and levels of protection. In some embodiments, pattern for the electrode can be formed by de-alloying the conduct layer to increase surface anomalies. For example, selective leaching can be used to remove selectively one element from an alloy (e.g., a corrosion processes). The pattern can also be formed by stamping, chemical etch, or other surface removal processes.

Figure 9:
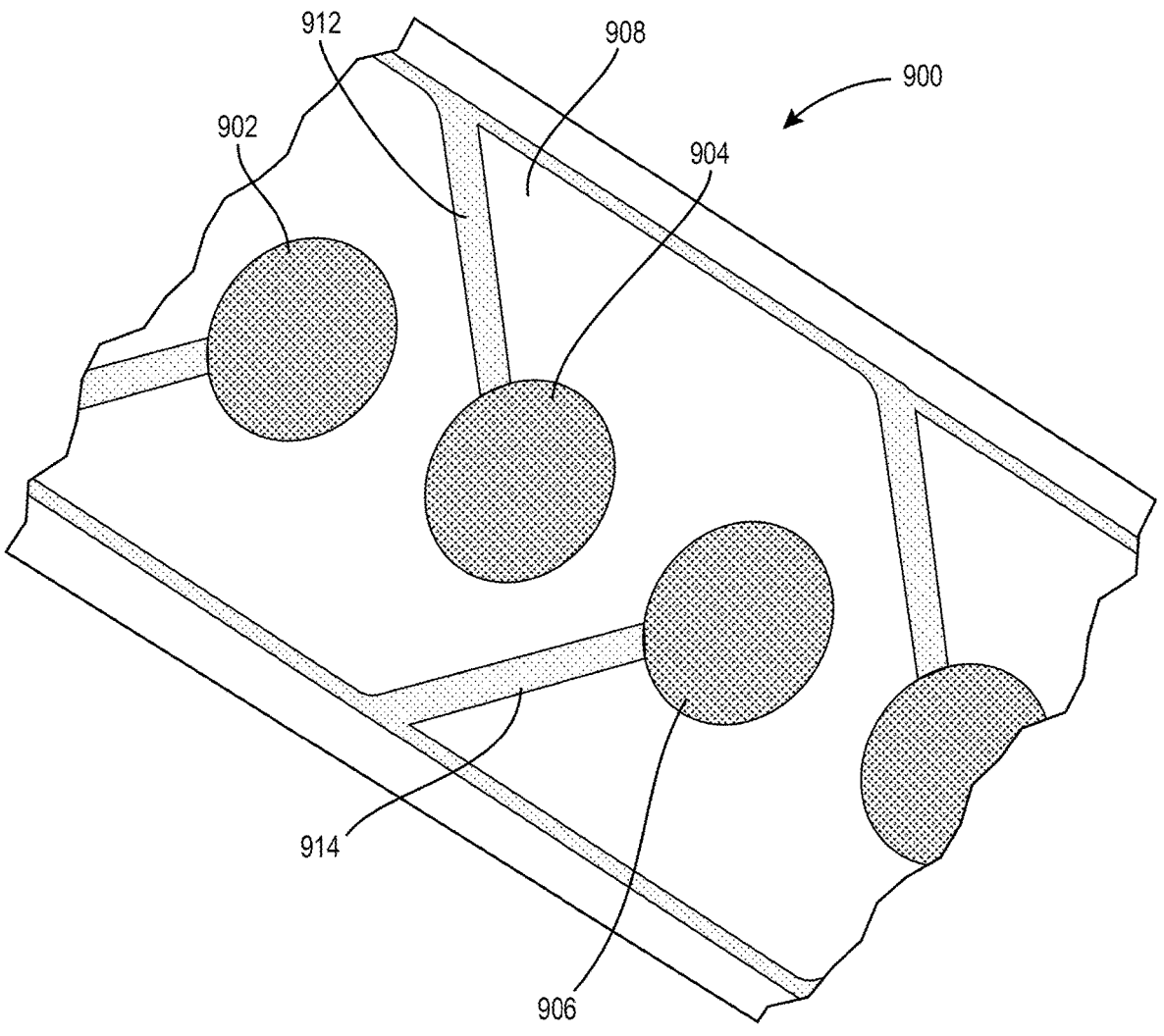
FIG. 9 is a top planar view schematic drawing of a set of electrodes for a catheter according to some embodiments.
Figure 10:
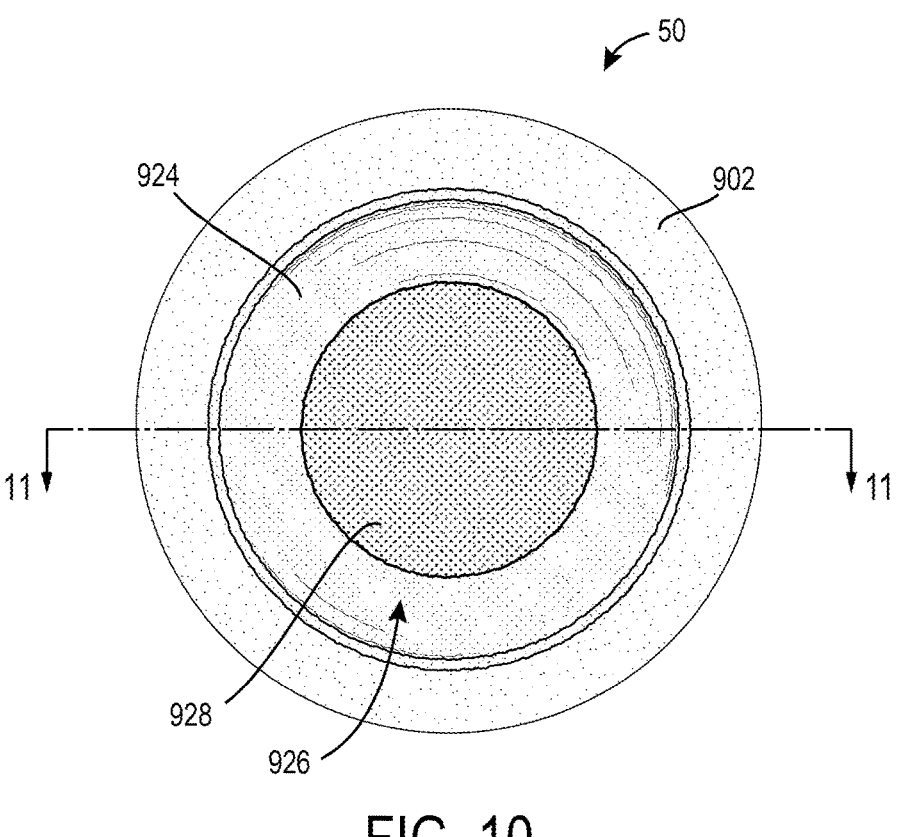
FIG. 10 is a top planar view schematic drawing of one of the electrodes illustrated in FIG. 9 according to some embodiments.

With reference to FIGS. 9-10, a set 900 of electrodes 902, 904, and 906 are disposed on a flex circuit 908 and can be attached at the tip portion 106 of catheter 102 (FIG. 1) in some embodiments. Printed wire conductors or conductive traces 912 and 914 can be in communication with ECU 142 (FIG. 1) and connect to electrodes 904 and 906, respectively. Electrodes 902, 904 and 906 can be used to provide or receive electrical signals in catheter applications. Electrodes 902, 904, and 906 include a recessed center portion 926 as described below with reference to FIGS. 9-11.

Electrode 902 includes a ridge 924 defining a recessed center portion 926. An impedance reduction layer 928 is disposed in the recessed center portion 926. In FIG. 10, an X-axis 932 defines cross sectional lateral distance along line 10-10 in FIG. 10 in millimeters, and a Y-axis 930 defines cross sectional vertical distance along line 10-10 in FIG. 9 in microns.

The recessed portion 926 has a depth of 9 microns and a top surface of the impedance reduction layer 928 is 4 microns below a top surface of ridge 924. The impedance reduction layer 928 has a surface area of approximately one ninth of the surface area of the electrode 902 (e.g., the electrode 902 is approximately 11 percent covered by the impedance reduction layer 928). In some embodiments, the impedance reduction layer 928 covers between 90 percent and 8 percent of the exposed surface area or contact surface area of the electrode 902. The extension of the ridge 924 above the top surface of the impedance reduction layer 928 provides protection for the impedance reduction layer 928.

In some embodiments, the electrode 902 is formed by masking and etching metal material in the shape of electrode 902. Uneven gold distribution above the metal material is used to form the edge or ridge 924 and the recessed portion 926. Masking can be used to define the ridge 924 of gold material in some embodiments. Other materials can also be utilized.

Figure 12:
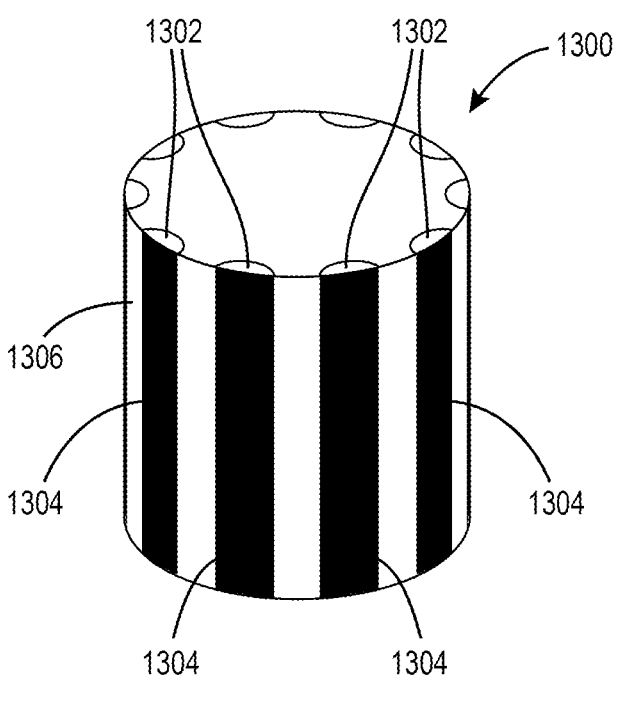
FIG. 12 is a perspective view schematic drawing of a ring electrode for a catheter according to some embodiments.

With reference to FIG. 12, a ring electrode 1300 can be used as one of electrodes 208 (FIG. 2). Ring electrode 1300 includes recessed portions 1302. The recessed portions 1302 include impedance reduction layer 1304. The recessed portions 1302 are machine grooves, etched grooves, or laser formed grooves in some embodiments. The ring electrode 1300 can be coupled to a wire for connection to ECU 142, ablation generator 122 or other component of system 10.

Although shown as vertical grooves in FIG. 12, recessed portions 1302 are diagonal grooves or grooves in other patterns in some embodiments. In some embodiments, the grooves are V-shaped or U-shaped in cross-section. The impedance reduction layer 1304 is protected by the native material of the electrode 1300 due to the disposition of the impedance reduction layer 1304 in the recessed portions 1302 as the impedance reduction layer 1304 is below the outer surface 1306 of the ring electrode 1300. In some embodiments, the recessed portions 1302 have a depth of 2-60 microns (e.g., 5 microns) from the outer surface 1306, and the impedance reduction layer 1304 is between 1 micron and 30 microns (e.g., between 1 and 5 microns) thick. In some embodiments, the difference between the depth of the recessed portions 1302 and the thickness of the impedance reduction layer 1304 is 1 to 30 microns such that the outer surface 1306 is 1 to 30 microns (e.g., 4 microns) above the impedance reduction layer 1304.

Figure 13:
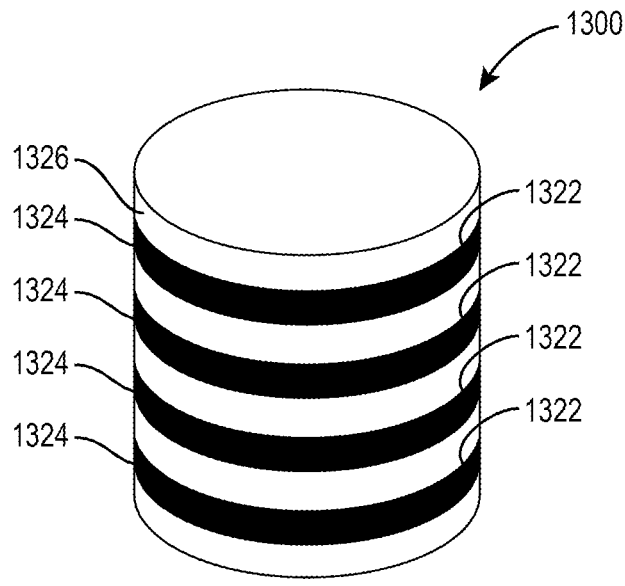
FIG. 13 is a perspective view schematic drawing of a ring electrode for a catheter according to some embodiments.

With reference to FIG. 13, a ring electrode 1320 can be used as one of electrodes 208 (FIG. 2) and is similar to ring electrode 1300. Ring electrode 1320 includes recessed portions 1322. The recessed portions 1322 contain the impedance reduction layer 1324. The recessed portions 1322 are machine grooves or laser formed grooves in some embodiments. In some embodiments, the recessed portions 1322 have a depth of 2-60 microns (e.g., 5 microns) from the outer surface 1326, and the impedance reduction layer 1324 is between 1 micron and 30 microns (e.g., between 1 and 5 microns) thick. In some embodiments, the difference between the depth of the recessed portions 1322 and the thickness of the impedance reduction layer 1324 is 1 to 30 microns such that the outer surface 1326 is 1 to 30 microns (e.g., 4 microns) above the impedance reduction layer 1324.

Figure 14:
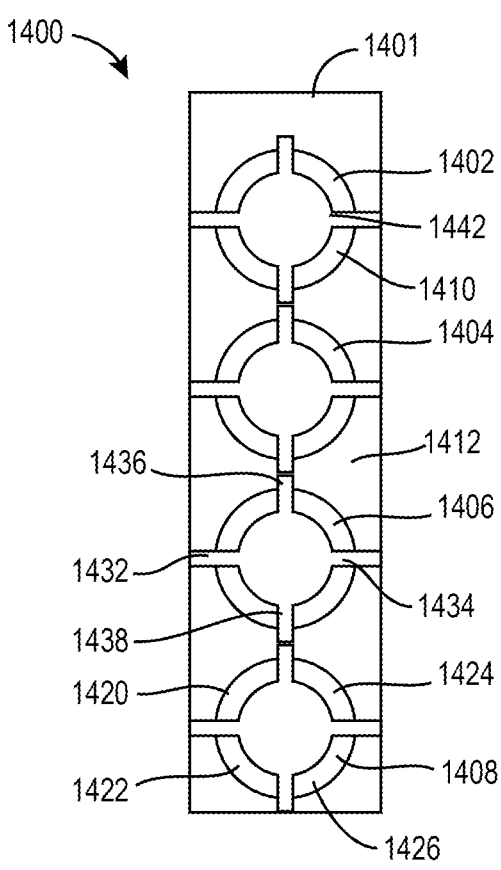
FIG. 14 is a top planar view schematic drawing of a set of electrodes for a catheter according to some embodiments.

With reference to FIG. 14, a set 1400 of electrodes 1402, 1404, 1406, and 1408 can be part of a flex circuit disposed on a flex substrate 1401 and can be attached at the tip portion 106 of catheter 102 (FIG. 1) in some embodiments. In some embodiments, electrodes 1402, 1404, 1406, and 1408 are provided on a Kapton ° tape substrate manufactured by DuPont de Nemours, Inc. or other flex substrate 1401. The flex circuit substrate 1401 can be polyimide, polyester, polyethylene terephthalate, polyethylene naphthalate, polyetherimide, various fluoropolymers, copolymers, or other suitable flexible substrate material. The electrodes 1402, 1404, 1406, and 1408 each include an impedance reduction layer provided at a center portion of each of electrodes 1402, 1404, 1406, and 1408. Printed wire conductors or conductive traces can be in communication with ECU 142 (FIG. 1) and connect to electrodes 1402, 1404, 1406, and 1408. Electrodes 1402, 1404, 1406, and 1408 can be used to provide or receive electrical signals in catheter applications.

Electrodes 1402, 1404, 1406, and 1408 each include a recessed center portion within an outer edge 1410 of each of electrodes 1402, 1404, 1406, and 1408. The recessed portion can be similar to recessed center portion 926 (FIG. 9). The recessed portion has a depth of 7-12 microns and a top surface of the impedance reduction layer is 3-5 microns below a top surface of outer edge 1410 in some embodiments. The impedance reduction layer can be similar to impedance reduction layer 928 (FIG. 9) and can have a surface area less than the surface area of each of electrodes 1402, 1404, 1406, and 1408. The impedance reduction layer can be provided in each center portion (e.g., having approximately one ninth of the surface area of each of electrodes 1402, 1404, 1406, and 1408). In some embodiments, the impedance reduction layer covers between 90 percent and 8 percent of the exposed surface area or contact surface area of each electrodes 1402, 1404, 106, and 1408. The extension of the outer edge 1410 above the top surface of the impedance reduction layer provides protection for the impedance reduction layer. The center portion as well as the outer edge 1410 can be patterned as described with reference to FIGS. 6, 7, and 8 to provide additional protection for the impedance reduction layer.

During manufacture, flex substrate 1401 is covered by a mask 1412. Mask 1412 can be a strip of Kapton tape or other suitable material for masking the center portion of each of electrodes 1402, 1404, 1406, and 1408. In some embodiments, the electrodes 1402, 1404, 1406, and 1408 are formed by masking and etching metal material in the shape of electrodes 1402, 1404, 1406, and 1408. The metal material can be a copper, copper alloy, or other conductive material and have a relatively planar top surface. Mask 1412 is provided over the metal material and includes exposed portions 1422, 1424, 1426 and 1428 for each of electrodes 1402, 1404, 1406, and 1408.

The mask 1412 includes segments 1432, 1434, 1436, and 1438 provided over outer edge 1410. The particular pattern of mask 1412 shown in FIG. 14 is exemplary. Segments 1432, 1434, 1436, and 1438 can act as struts or support members for holding a center mask portion 1442 associated with the recessed center portion in place. The pattern associated with segments 1432, 1434, 1436, and 1438 of mask 1412 can have various configurations including configurations with fewer or more segments. Other support configurations which do not use segments 1432, 1434, 1436, and 1438 can be utilized to hold center mask portion 1442 in place.

Figure 11:
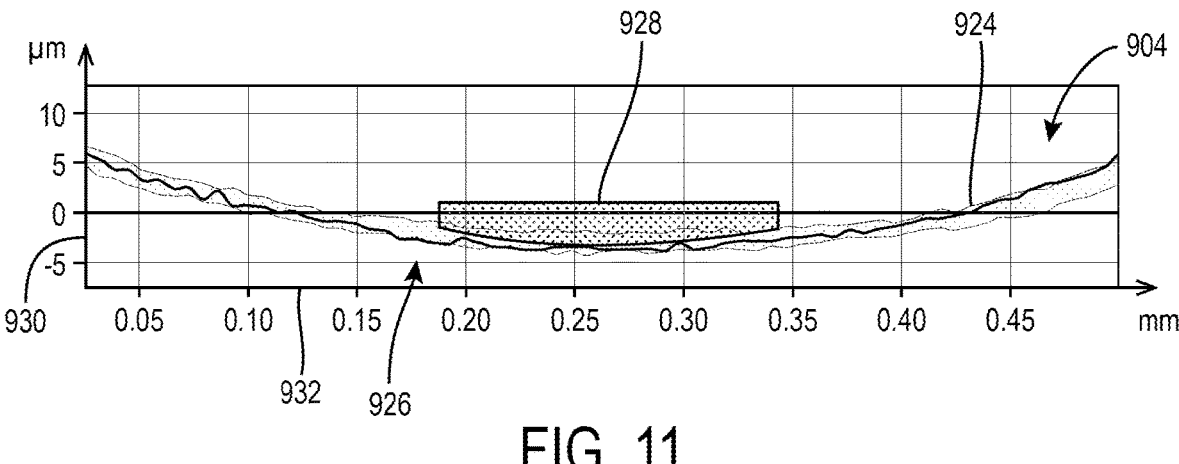
FIG. 11 is a cross-sectional view schematic drawing of the electrode illustrated in FIG. 9 about line 11-11 according to some embodiments.

After the mask 1412 is applied, electrodes 1402, 1404, 1406, and 1408 are plated, thereby creating a thicker outer edge 1410 than the recessed center portion. Copper, gold, and other metal plating techniques can be utilized. The plating operation results in a cupped shape for the electrodes 1402, 1404, 1406, and 1408 such that outer edge 1410 is raised above the recessed center portion and provides protection for the impedance reduction layer (e.g., similar to electrode 902 (FIGS. 9-11). In some embodiments, electrodes 1402, 1404, 1406, and 1408 have a U-shaped cross section, and the recessed center portion is fully or partially coated with the impedance reduction layer. The portions under segments 1432, 1434, 1436, and 1438 can also be recessed. After plating, mask 1412 is removed and the impedance reduction layer can be applied. The impedance reduction layer can be applied across the entire top surface of electrodes 1402, 1404, 1406, and 1408 and removed mechanically or chemically from the outer edge 410 of each of electrodes 1402, 1404, 1406, and 1408 (e.g., by etching, a chemical mechanical polish, a mechanical polish, or other technique). The impedance reduction layer can remain disposed at the locations of segments 1432, 1434, 1436, and 1438 in some embodiments.

Figure 15:
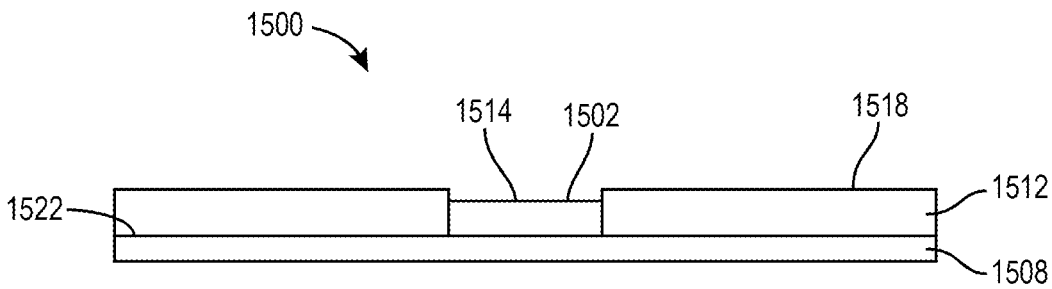
FIG. 15 is a cross-sectional view schematic drawing of an electrode for a catheter according to some embodiments.

With reference to FIG. 15, an electrode 1502 is disposed on a flex substrate 1508 which can be used as flex circuit and can be attached at the tip portion 106 of catheter 102 (FIG. 1) in some embodiments. In some embodiments, electrode 1502 is provided on a Kapton tape strip or flex substrate 1508 covered by a mask 1512. The flex substrate 1508 can be polyimide, polyester, polyethylene terephthalate, polyethylene naphthalate, polyetherimide, various fluoropolymers, copolymers, or other suitable flexible substrate material. Mask 1512 can be a Kapton tape or other suitable material for protecting electrode 1502. Mask 1512 can be made of a similar material to the material of flex substrate 1508. Printed wire conductors or conductive traces can be in communication with ECU 142 (FIG. 1) and connect to electrode 1502. Electrode 1502 can be used to provide or receive electrical signals in catheter applications. Mask 512 and substrate 1508 are 20-200 microns thick in some embodiments.

In some embodiments, a top surface 1514 of electrode 1502 is below a top surface 1518 of mask 1512. In some embodiments, mask 1512 is thicker than electrode 1502. Substrate 1508 is half as thick as mask 1512 in some embodiments. The mask 1512 is 3-12 microns thicker than electrode 1502 in some embodiments. An impedance reduction layer similar to impedance reduction layer 928 (FIG. 9) is provided at the top surface 1514 of electrode 1502. In some embodiments, the difference in thickness is between 2-60 microns (e.g., 5 microns) from the impedance reduction layer at the top surface 1514 of the electrode 1502 to the top surface 518.

The impedance reduction layer is between 1 micron and 30 microns (e.g., between 1 and 5 microns) thick in some embodiments. Electrode 1502 with the impedance reduction layer is 18 to 170 microns thick in some embodiments. In some embodiments, the impedance reduction layer covers between 100 percent and 8 percent of the exposed surface area or contact surface area of the electrode 1502. The mask 1512 which extends above the top surface of the impedance reduction layer on the electrode 1502 provides protection for the impedance reduction layer. The electrode 1502 can be patterned as described with reference to FIGS. 6, 7, and 8 to provide additional protection for the impedance reduction layer.

In some embodiments, the mask 1512 is applied to a top surface 1522 of substrate 1508 after electrode 1502 is formed and the impedance reduction layer is applied. In some embodiments, the mask 1512 is applied to the top surface 1522 of substrate 1508 after electrode 1502 is formed and before the impedance reduction layer is applied. In some embodiments, the mask 1512 is applied to the top surface 1522 of substrate 1508 before electrode 1502 is formed and before the impedance reduction layer is applied. A plating operation for electrode 1502 can be provided before or after mask 1512 is applied. Mask 1512 can be secured to substrate 1508 by an adhesive or in a lamination process. The combination of mask 1512 and substrate 1508 forms a sandwich structure which protects the embedded or counter-sunk electrode 1502 in some embodiments. Mask 1512 is a protective layer for preventing abrasion of the electrode 1502 in some embodiments.

Various embodiments (examples) are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter comprising:
   a shaft including a proximal end and a distal end;
   an electrical conductor extending along the shaft; and
   an electrode disposed along the distal end of the shaft and coupled to the electrical conductor, the electrode comprising:
   at least one recessed portion defined by a respective at least one metal edge; and
   an impedance reduction layer disposed in the at least one recessed portion, wherein the impedance reduction layer has a thickness less than a depth of the recess portion;
   wherein the impedance reduction layer is a conductive polymer based coating; and
   wherein the impedance reduction layer and the respective at least one metal edge of the electrode are configured to contact tissue.

2. The catheter of claim 1, wherein the electrode is a diagnostic electrode.

3. The catheter of claim 1, wherein the electrode is a therapy or stimulation electrode.

4. The catheter of claim 1, further comprising a flexible circuit including the electrical conductor and the electrode, wherein the flexible circuit is attached to or integrated into the catheter.

5. The catheter of claim 1, wherein the at least one recessed portion is formed by laser etching, lithographically etching, machining, additive manufacturing, a deposition process, or an impression-based process.

6. The catheter of claim 1, wherein the impedance reduction layer comprises poly(3,4-ethylenedioxythiophene):poly (styrenesulfonate) (PEDOT:PSS) or poly(3,4-ethylenedi-oxythiophene):p-tosylate (PEDOT).

7. The catheter of claim 1, wherein the depth of the at least one recessed portion is at least 5 microns and wherein the thickness of the impedance reduction layer is less than 5 microns.

8. The catheter of claim 1, wherein the electrode is a ring electrode, the at least one recessed portion is a groove in the electrode, and the electrical conductor is a wire.

9. The catheter of claim 8, wherein the groove is U-shaped or V-shaped in cross section.

10. The catheter of claim 1, wherein the electrical conductor is a trace positioned along a flexible circuit and the electrode is provided on the flexible circuit.

11. The catheter of claim 9, wherein the at least one recessed portion is repeated as a pattern across a surface area of the electrode.

12. A method of making a catheter, the method comprising:

coupling an electrical conductor and an electrode to the catheter, the electrode having at least one recessed portion defined by a respective at least one metal edge; and disposing an impedance reduction layer in the at least one recessed portion of the electrode, wherein the impedance reduction layer has a thickness less than a depth of the recessed portion;

wherein the impedance reduction layer is a conductive polymer based coating; and wherein the impedance reduction layer and the respective at least one metal edge of the electrode are configured to contact tissue.

13. The method of claim 12, wherein the impedance reduction layer covers less than all of a surface area of the electrode.

14. The method of claim 12, wherein the at least one recessed portion is repeated as a pattern across a surface area of the electrode.

15. The method of claim 12, wherein coupling the electrical conductor and the electrode to the catheter further comprises attaching a flexible circuit including the electrical conductor and the electrode to the catheter or integrating the flexible circuit including the electrical conductor and the electrode into the catheter.

16. The method of claim 12, wherein the at least one recessed portion is an area between cylindrical extensions on a surface of the electrode.

17. The method of claim 12, wherein the at least one recessed portion is formed by laser etching, lithographically etching, machining, additive manufacturing, a deposition process, or an impression-based process.

18. The method of claim 17, wherein the respective plurality of metal edges are formed by masking a central portion of the electrode and plating an exposed portion.

19. The method of claim 18, wherein the electrode is formed on a flexible substrate.

* * * * *